United States Patent
Zierenberg et al.

(10) Patent No.: US 6,689,092 B2
(45) Date of Patent: Feb. 10, 2004

(54) NEEDLE-LESS INJECTOR OF MINIATURE TYPE

(75) Inventors: Bernd Zierenberg, Bingen am Rhein (DE); Ralph Christian Reimholz, Wiesbaden (DE); Knut Elbers, Gau Algesheim (DE); Stefan Henke, Gau-Odernheim (DE); Joachim Eicher, Dortmund (DE); Johannes Geser, Ingelheim (DE)

(73) Assignee: Boehringer International GmbH (DE)

( * ) Notice: Subject to any disclaimer, the term of this patent is extended or adjusted under 35 U.S.C. 154(b) by 0 days.

(21) Appl. No.: 09/797,001

(22) Filed: Mar. 2, 2001

(65) Prior Publication Data

US 2002/0058908 A1 May 16, 2002

Related U.S. Application Data

(60) Provisional application No. 60/197,405, filed on Apr. 14, 2000.

(30) Foreign Application Priority Data

Mar. 3, 2000 (DE) .......................... 100 10 123

(51) Int. Cl.$^7$ ............................... H61M 5/30
(52) U.S. Cl. ........................... 604/68; 604/72
(58) Field of Search ............... 604/68, 69, 70, 604/71, 72, 87, 131, 134, 135

(56) References Cited

U.S. PATENT DOCUMENTS 3,802,430 A * 4/1974 Schwebel et al. ............. 604/69
5,062,830 A * 11/1991 Dunlap ........................ 604/68

(List continued on next page.)

FOREIGN PATENT DOCUMENTS

| DE | 25 51 992 | 8/1976 |
| DE | 30 30 671 | 3/1981 |

(List continued on next page.)

OTHER PUBLICATIONS

Derwent Information, "Medication Metering Distributor for Hypodermic–Has dosing unit on flexible wall transmitting power pulses," Abstract for DE 2551992, publication date unknown.

Derwent Information, "Percutaneous injection pistol partic. for rapid mass vaccination—discharges high velocity liq. jet by trigger release of loaded spring," Abstract for DE 3030671, publication date unknown.

(List continued on next page.)

*Primary Examiner*—Thor Campbell
(74) *Attorney, Agent, or Firm*—Sterne, Kessler, Goldstein & Fox P.L.L.C.

(57) ABSTRACT

Needle-less injectors for liquids are known in many different forms which are adapted to different conditions of use. The needle-less injector according to the invention is in the form of a hand-held unit. It includes a locking stressing mechanism, an energy-storing spring (36), a hollow plunger (37) displaceable in a cylinder (38) and a nozzle (39). At its one end, the hollow plunger is provided with a valve body (42). The supply container (44) for the liquid is arranged within the housing. When the locking stressing mechanism is stressed by rotation of the two housing portions (31, 32) relative to each other the hollow plunger (37) is drawn out of the cylinder (38); at the same time the amount of liquid required for an injection is conveyed out of the supply container (44) through the plunger into the pump chamber (43). After the locking stressing mechanism is triggered the amount of liquid is expelled from the pump chamber through the nozzle. The needle-less injector can be safely and easily handled, even by unskilled persons. It is used for the intracutaneous injection of a medicament-bearing liquid into biological tissue, for the injection of an active substance-bearing liquid into a plant, or for the injection of a liquid through a membrane into the space behind the membrane.

39 Claims, 3 Drawing Sheets

U.S. PATENT DOCUMENTS

| | | | | |
|---|---|---|---|---|
| 5,503,627 A | * | 4/1996 | McKinnon et al. | 604/68 |
| 5,846,233 A | * | 12/1998 | Lilley et al. | 604/411 |
| 5,899,879 A | * | 5/1999 | Umbaugh | 604/68 |
| 5,964,416 A | * | 10/1999 | Jaeger et al. | 222/383.1 |

FOREIGN PATENT DOCUMENTS

| | | |
|---|---|---|
| EP | 0 675 762 B1 | 9/1994 |
| WO | 90/04989 | 5/1990 |
| WO | 93/03779 | 3/1993 |
| WO | 97/47341 | 12/1997 |

OTHER PUBLICATIONS

Derwent Information, "Method and appts. for grinding of old brasques and similar products—comprises crushing operation, screening operation to separate from the crushed product the grains having the dimensions of the finished prod., and a grinding operation to reduce the crushed product to required dimensions.," Abstract of EP 675762, publication date unknown.

* cited by examiner

NEEDLE-LESS INJECTOR OF MINIATURE TYPE

BACKGROUND OF THE INVENTION

1. Field of the Invention

The invention concerns a needle-less injector in the form of a hand-held unit, preferably of miniature type, with which a liquid is intracutaneously injected for example into human or animal tissue. The invention aims to expand the area of use of an injector of that kind.

2. Related Art

Liquids in the sense of the present invention are preferably solutions, suspensions or dispersions which contain an active substance. Active substances can be pharmacologically active substances for treatment of the human or animal body or they may be substances for diagnostic or cosmetic uses.

Active substances for non-pharmaceutical uses can be, for example, in the area of plant protection insecticides, fungicides, growth-promoting or growth-inhibiting agents or fertilizers. The needle-less injector according to the invention permits the environmentally friendly application of agents with a systemic action, as the active substance is applied directly to the plant.

EP 0 063 341 and EP 0 063 342 disclose a needle-less injector which includes a piston pump for expelling the liquid to be injected, which is driven by a motor by means of a pressure agent. The liquid container is mounted laterally to the piston pump. The amount of liquid required for an injection is sucked into the pump chamber by way of an inlet passage and a flap check valve when the piston is retracted. As soon as the piston is moved in the direction of the nozzle body the liquid is urged through the outlet passage to the nozzle and expelled. The piston of the piston pump is a solid round piston.

EP 0 133 471 describes a needle-less vaccination unit which is operated with carbon dioxide under pressure, from a siphon cartridge by way of a special valve.

EP 0 347 190 discloses a vacuum compressed gas injector in which the depth of penetration of the injected drug can be adjusted by means of the gas pressure and the volume of the drug can be adjusted by way of the piston stroke.

EP 0 427 457 discloses a needle-less hypodermic syringe which is operated by means of compressed gas by way of a two-stage valve. The injection agent is disposed in an ampoule which is fitted into a protective casing secured to the injector housing. The ampoule is fitted on to the end of the piston rod. Disposed at the other end of the ampoule is the nozzle whose diameter decreases towards the end of the ampoule.

WO 89/08469 discloses a needle-less injector for one-off use. WO 92/08508 sets forth a needle-less injector which is designed for three injections. The ampoule containing the drug is screwed into one end of the drive unit, with the piston rod being fitted into the open end of the ampoule. At its one end, the ampoule contains the nozzle through which the drug is expelled. A displaceable closure plug is provided approximately at the center of the length of the ampoule. The dose to be injected can be adjusted by changing the depth of the ampoule. The piston rod which projects from the drive unit after actuation of the injector is pushed back by hand. Both units are operated with compressed gas.

WO 93/03779 discloses a needle-less injector with a two-part housing and a liquid container which is fitted laterally to the unit. The drive spring for the piston is stressed by means of a drive motor. The spring is released as soon as the two parts of the housing are displaced relative to each other by pressing the nozzle against the injection location. Respective valves are provided in the intake passage for the liquid and in the outlet of the metering chamber.

WO 95/03844 discloses a further needle-less injector. It includes a liquid-filled cartridge which at one end includes a nozzle through which the liquid is expelled. At the other end the cartridge is closed by a cap-type piston which can be pushed into the cartridge. A piston which is loaded by a prestressed spring, after release of the spring, displaces the cap-type piston into the cartridge by a predetermined distance, with the amount of liquid to be injected being expelled in that case. The spring is triggered as soon as the nozzle is pressed sufficiently firmly against the injection location. This injector is intended for one-off or repeated use. The cartridge is arranged in front of the spring-loaded piston and is a fixed component of the injector. The position of the piston of the injector which is intended for a plurality of uses is displaced after each use by a distance in a direction towards the nozzle. The piston and the drive spring cannot be reset. The prestressing of the spring is initially sufficiently great to expel the entire amount of liquid in the cartridge all at once. The spring can only be stressed again if the injector is dismantled and the drive portion of the injector assembled with a fresh, completely filled cartridge.

In some known design configurations of the needle-less injector the supply container for the liquid to be injected is arranged laterally beside the drive unit. The amount of liquid to be injected is sucked into the pump chamber when the solid piston of the piston pump is retracted. The inlet passage includes an inlet valve and the outlet passage includes an outlet valve. Both valves operate with an auxiliary force.

In other design configurations of the needle-less injector the supply container for the liquid to be injected serves directly as a pump chamber and is subjected to the sudden application of force which occurs upon expulsion of the amount of liquid to be injected.

In the case of the needle-less injectors which are operated with compressed gas, a part of the compressed gas escapes after each injection. The compressed gas container is possibly replaceable but it cannot be directly filled with compressed gas again. With such injectors, the drive unit has to be replaced as soon as the compressed gas container is empty.

Accordingly the object is that of providing a multi-use needle-less injector of a simple design, which is preferably suited for repeated expulsion of a predetermined amount of liquid. The amount of liquid which is expelled overall after many uses should preferably be greater than the amount of liquid contained in a supply container. It should be possible for either a plurality of partial amounts of the liquid to be successively dispensed from the supply container or for the amount of liquid contained in a supply container to be taken as a whole and expelled all at once. The supply container should be able to be replaced in a simple manner. A sufficiently great mechanical thrust force (impulse) is to be imparted to the predetermined amount of liquid so that the predetermined amount of liquid penetrates a membrane, a foil or biological tissue.

SUMMARY OF THE INVENTION

In accordance with the invention that object is attained by a needle-less injector for a liquid, which is arranged in the form of a hand-held unit in a cylindrical housing and which includes a supply container for the liquid. The housing substantially comprises two portions. The two portions are releasably or non-releasably connected together and are arranged rotatably relative to each other. The needle-less injector includes a locking stressing mechanism for a spring-actuated drive, which is stressed prior to the expulsion of a predetermined amount of the liquid and which is provided with a triggering device. Fixed in the sprung portion of the locking stressing mechanism is a hollow plunger which is driven by the locking stressing mechanism. The hollow plunger is arranged slidably within a cylinder. It projects with its one end out of the cylinder. Preferably at its other end there is mounted a valve body which is the single valve body of the needle-less injector. A nozzle with at least one opening is disposed at the end of the cylinder. The space between the nozzle and the end of the hollow plunger is the pump chamber. A supply container for the liquid is provided within the housing. The supply container is in the form of a container which is separate from the needle-less injector and which—preferably by means of a press fit—is releasably connected to the end of the hollow plunger which projects out of the cylinder. The predetermined amount of the liquid which has been conveyed into the pump chamber upon retraction movement of the sprung portion and the hollow plunger connected thereto, through the hollow plunger, is determined by the stroke movement and the cross-section of the hollow plunger.

DETAILED DESCRIPTION OF THE INVENTION

Figure 1:
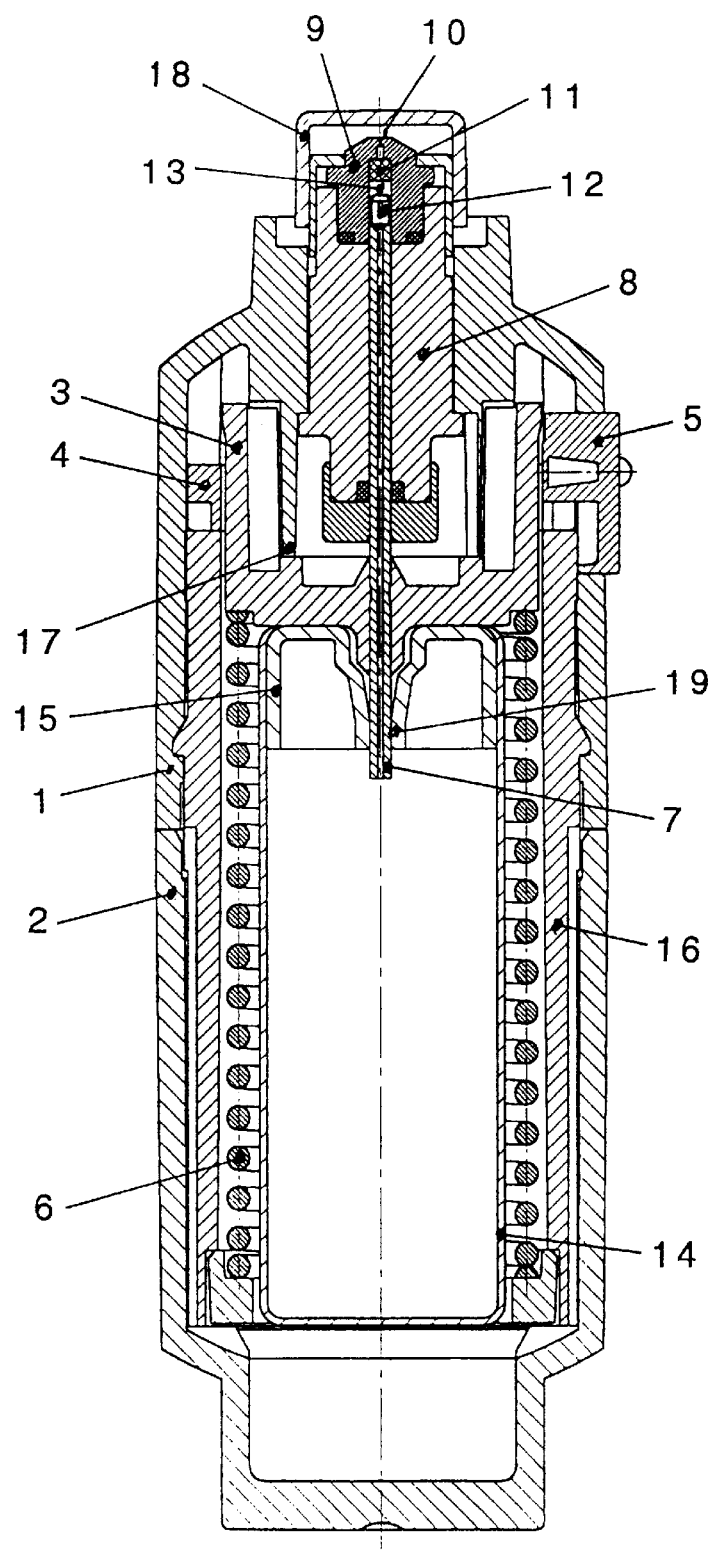
FIG. 1 is a sectional view of an embodiment of the needle-less injector of the present invention in a rest condition.

The locking stressing mechanism comprises a spring-loaded drive flange as the sprung portion, a drive for stressing the spring, a locking member, two abutments for the drive flange, between which the drive flange can move with a reciprocating movement, and a device for triggering the locking member. The travel of the drive portion is limited precisely by the two abutments. A force-transmitting transmission arrangement is disposed between the energy-storing spring and the drive for stressing the spring. The locking member is annular and has interengaging locking surfaces. A preferably cylindrical coil spring or a disk spring or a leaf spring, which acts as a tension spring or as a compression spring, can be used as the energy storage means.

The energy-storing spring can be stressed by means of a direct drive. For that purpose the drive flange is displaced by an axially acting external force. When a high level of spring force is involved, a force-stepup transmission arrangement is advantageous, for example a worm-thrust transmission arrangement, by means of which the spring is stressed by an external torque. A transmission arrangement of that kind is a single-speed or multi-speed transmission arrangement which is disposed between the spring and the drive for stressing the spring.

The drive flange can be of a cup-shaped configuration. The collar of the drive flange may include for example two sawtooth-shaped openings, against which two sawteeth in the upper part of the housing slide.

The average spring force can be between 10 N and 150 N. Between the two positions of the sprung portion of the locking stressing mechanism the spring force changes approximately by ±10% of the average spring force.

The locking member can be a ring which in itself is radially elastically deformable, or a rigid ring with displacement projections, or a rigid ring with leaf springs formed thereon, or a ring which is subjected to prestressing by one or more metal springs. The ring can be closed or open; it can comprise a plurality of portions. The locking member is arranged displaceably in a plane perpendicular to the axis of the housing, or it is deformable in that plane.

Further details relating to the locking stressing mechanism for a spring-actuated drive are described in DE 195 45 226.

Fixed in the sprung portion of the locking stressing mechanism is a hollow plunger which is driven by the locking stressing mechanism. The hollow plunger engages into the cylinder and projects with a part of its length out of the cylinder; it is arranged slidably within the cylinder.

A nozzle is fitted to the end of the cylinder. The nozzle opening can have a hydraulic diameter of from 10 $\mu$m to 500 $\mu$m, preferably from 50 $\mu$m to 150 $\mu$m. The nozzle opening can involve a length of from 50 $\mu$m to 500 $\mu$m, preferably 100 $\mu$m to 300 $\mu$m.

When there are a plurality of openings in the nozzle the longitudinal axes of the nozzle openings can extend in mutually parallel relationship or they can be inclined divergently relative to each other. When the nozzle has a plurality of openings the hydraulic diameter thereof can be different.

The nozzle can comprise a parallelepiped which is composed of two silicon plates and which, for example, is 1.1 mm wide, 1.5 mm long and 2.0 mm high. In the contact surface between the plates the parallelepiped can have a shallow triangular opening which is about 400 $\mu$m thick and which terminates in a single nozzle opening which is 50 $\mu$m wide, 50 $\mu$m thick and 200 $\mu$m long. It may be desirable for the nozzle to be surrounded over its entire periphery with an accurately fitting elastomer shaped portion. The internal contour of the elastomer shaped portion is matched to the external contour of the nozzle and the external contour of the elastomer shaped portion is matched to the internal contour of a nozzle holder which preferably comprises metal. A 'floating mounting' of that kind means that the nozzle which is of brittle material is insensitive to loadings which act in a shock-like fashion and which occur in regular use of the needle-less injector.

A valve body which preferably consists of one piece is mounted preferably to the end of the hollow plunger which is disposed within the cylinder, which valve body is guided through the hollow plunger and is arranged axially displaceably with respect to the hollow plunger. The valve body moves substantially with the hollow body. The valve body is preferably of a shape which is rotationally symmetrical about a single axis, such as for example a circular cylinder or a truncated cone. Its diameter can be smaller than the diameter of the space in which the valve body is displaceably arranged. The valve body can rotate about its axis. The axis of the valve body always remains parallel to the axis of the hollow plunger. That therefore affords a defined sealing surface on the inlet side of the valve body. The distance over which the valve body can be displaced relative to the hollow plunger is limited by an abutment. The valve is closed in the position in which the valve body bears against the defined sealing surface.

The space between the nozzle and the valve body mounted to the hollow plunger is the pump chamber. It is possible to arrange a filter which is preferably in the form of a depth filter in front of the nozzle end of the pump chamber, that is to say in the expulsion passage for the liquid. If the liquid to be injected contains suspended particles the pore size of the filter is to be adapted to the particle size.

Further details relating to the hollow plunger and the valve body are set forth in DE 195 36 902.

The locking stressing mechanism and the energy-storing spring are preferably stressed relative to each other by rotation of the two housing portions, preferably by way of a worm-thrust transmission arrangement. The torque can be produced by hand or by means of a motor.

The cylinder diameter is preferably practically identical over its entire length to the outside diameter of the hollow plunger. The cylinder can be fixedly mounted in the one portion of the housing. In addition the cylinder can be axially displaceably mounted in the one portion of the housing. The displaceable cylinder is held in its rest position by a return spring.

The two abutments for the sprung portion can be fixedly positioned in the housing. Furthermore the position of one of those abutments can be variable in the axial direction. In that way it is possible to alter the volume of the pump chamber while the outside diameter of the hollow plunger is constant. In an otherwise unaltered design configuration of the needle-less injector the amount of expelled liquid can be altered by varying the position of an abutment.

The position of the travel movement of the sprung portion and thus the stroke movement of the hollow plunger within the needle-less injector is delimited by the two abutments. With a given position for the abutments the position of the travel movement of the sprung portion and therewith the stroke travel of the hollow plunger is constant for each injection.

The locking member is displaced parallel to the plane of the ring or is radially deformed in the plane of the ring, by means of a triggering device. When the cylinder is fixedly mounted in the housing the triggering device is actuated by means of a triggering button which can be depressed with a finger and the locking member is released. When the cylinder is mounted slidably in the housing the triggering device is actuated when the cylinder is pressed in against the force of the return spring and the locking member is disengaged.

A supply container for the liquid is provided within the housing. That supply container is in the form of a container which is separate from the needle-less injector; it is connected to the end of the hollow plunger which is in opposite relationship to the pump chamber. The end of the hollow plunger is covered by the liquid which is disposed in the supply container.

The supply container which is connected to the hollow plunger can additionally be connected to the sprung portion. That connection can be a releasable or non-releasable push-in connection in which the sprung portion is provided with a plurality of snap hooks which engage into a peripherally extending groove in the supply container after the supply container has been pushed into the needle-less injector.

The predetermined amount of the liquid to be expelled is determined by the stroke movement and the cross-section of the hollow plunger. The stroke movement of the hollow plunger is delimited by the two abutments for the drive flange.

It is desirable to provide in front of the nozzle a removable closure cap for protecting the nozzle opening during storage of the needle-less injector prior to and during the period of use thereof from contamination and evaporation of the liquid.

The two portions of the housing, the locking stressing mechanism, the cylinder and the supply container preferably comprise plastics material, for example polybutyleneterephthalate. The hollow plunger preferably comprises metal, for example high-quality steel.

The valve body can comprise metal, ceramic, glass, precious stone, plastics material or elastomer.

The nozzle can comprise metal, plastics material, glass, silicon or precious stone such as sapphire, ruby or corundum.

The filter preferably comprises sintered metal or sintered plastics material.

The needle-less injector is preferably produced in the form of a hand-held unit. It can be held and operated with one hand in the injection procedure. The cylinder, the hollow plunger, the valve body, the nozzle and possibly the filter are miniaturised components.

The mode of operation of the needle-less injector is described hereinafter.

During storage of the needle-less injector which has not been used or which has already been put to use and between two injections, the needle-less injector is in the rest condition. The energy-storing spring is in a prestressed condition. The sprung portion bears against the abutment which limits the travel of the sprung portion in the rest condition. The hollow plunger engages deeply into the cylinder. There is only a small spacing between the end of the hollow plunger and the inside of the nozzle. The locking member is in the disengaged position.

The locking stressing mechanism is stressed when the two housing portions are rotated relative to each other. The sprung portion is displaced in the axial direction away from the cylinder, in which case the stressing of the energy-storing spring is increased. At the same time the hollow plunger is pulled a distance out of the cylinder and the pump chamber is increased in size. The hollow plunger still projects with a part of its length into the cylinder. At the same time a part of the liquid contained in the storage container is conveyed through the hollow plunger and past the valve body into the pump chamber and the pump chamber is filled with liquid. The amount of liquid in the pump chamber is practically the same as the amount of liquid expelled during an injection. The sprung portion is displaced until the locking member jumps into its engaged position. In the case of a needle-less injector with a triggering button that button protrudes somewhat out of the housing.

The nozzle end of the needle-less injector is applied to and pressed against the injection location. In the case of a needle-less injector with triggering button the triggering button is actuated with a finger and pressed into the housing. In that way the locking member is pushed into the disengaged position and the injection is triggered. In the case of a needle-less injector with slidably arranged cylinder the injector is pressed with its nozzle end by hand with increasing force against the force of the return spring, against the injection location. In that situation the cylinder is pushed into the housing, the locking member is pushed into its disengaged position and the injection is triggered. When the needle-less injector is lifted off the injection location the return spring urges the cylinder back into its rest position.

As soon as the locking member has assumed the disengaged position the force K of the stressed energy-storing spring acts by way of the sprung portion, the hollow plunger and the closed valve at the end of the hollow plunger, during the period of time $\Delta t$, on the liquid in the pump chamber, whereby the mass of liquid m has imparted thereto the speed $\Delta v$ and thus a mechanical impulse $K \cdot t = m \cdot \Delta v$, and it issues from the nozzle at high speed and intracutaneously penetrates into the tissue. The needle-less injector is in the rest condition again after the injection.

The needle-less injector according to the invention can serve in human medicine and in veterinary medicine for the intracutaneous injection of a preparation, which is present in the form of a liquid, of an active substance, for example a drug, into human or animal tissue. Examples of suitable pharmaceutical preparations are inter alia analgesics, vaccines, anti-diabetic agents, hormones, contraceptives, vitamins, antibiotics, sedatives, antimicrobial substances, amino acids and coronary agents.

The preparation of the drug can be in the form of a solution, a suspension or an emulsion. In the case of suspensions the mean particle size should not exceed 15 $\mu$m, preferably 10 $\mu$m.

Suitable agents for dissolving, suspending or emulsifying active substances and possibly required additives are, for example, water, alcohols, alcohol-water mixtures and emulsions of oil in water or water in oil. They include purified, sterilised water, ethanol, propane diol, benzyl alcohols, ethanol-water mixtures, oils (such as coconut oil, peanut oil, soya oil, castor oil, sunflower oil), fatty acid esters (such as isopropyl myristate, isopropyl palmitate and ethyloleate), triglycerides, triacetin, solketal, and propylene glycol. The formulations may also contain additives such as for example preserving agents as well as acids or bases for adjusting the pH-value.

The predetermined amount of a liquid can be injected by means of the needle-less injector into a leaf or the stalk of a plant or through a membrane into the space behind the membrane.

The needle-less injector according to the invention enjoys the following advantages:

- It is of an easily manageable shape. The supply container for the liquid is disposed in the injector housing.
- It can be used for many—up to several hundred—injections which can be taken from one or more supply containers.
- Besides the valve at the end of the hollow plunger it does not have any further valves.
- The locking stressing mechanism can be easily handled, even when high spring forces are involved, by unskilled persons as well, and can be stressed with the application of a relatively small amount of force by way of a worm-thrust transmission arrangement.
- The locking stressing mechanism is triggered by hand by pressing a trigger button with a finger or when the needle-less injector is pressed against the injection location.
- The drive unit is not replaced but only the supply container for the liquid.
- The valve mounted at the end of the hollow plunger operates without ancillary force and closes very quickly.
- The volume of the pump chamber can be varied by varying the position of one of the two abutments.
- The mechanical impulse of the amount of liquid to be injected can be adapted to the desired depth of penetration into the tissue or to the thickness of the membrane to be penetrated.
- The supply container for the liquid is adapted to the conditions involved upon storage of the container—possibly for years—and to the connection thereof to the injector. Its design configuration is independent of the demands which are made on the pump chamber in front of the nozzle.
- The supply container for the liquid is not exposed to the thrust force upon injection.
- The supply container for the liquid can be replaced in a simple manner.
- The amount of liquid to be administered, which is required for a predetermined situation of use, can be successively injected at different locations in the injection region in a simple manner in a plurality of partial amounts.
- Needle-less injection has a substantially less adverse effect on the injection location than injection by means of an injection syringe.

Figure 2:
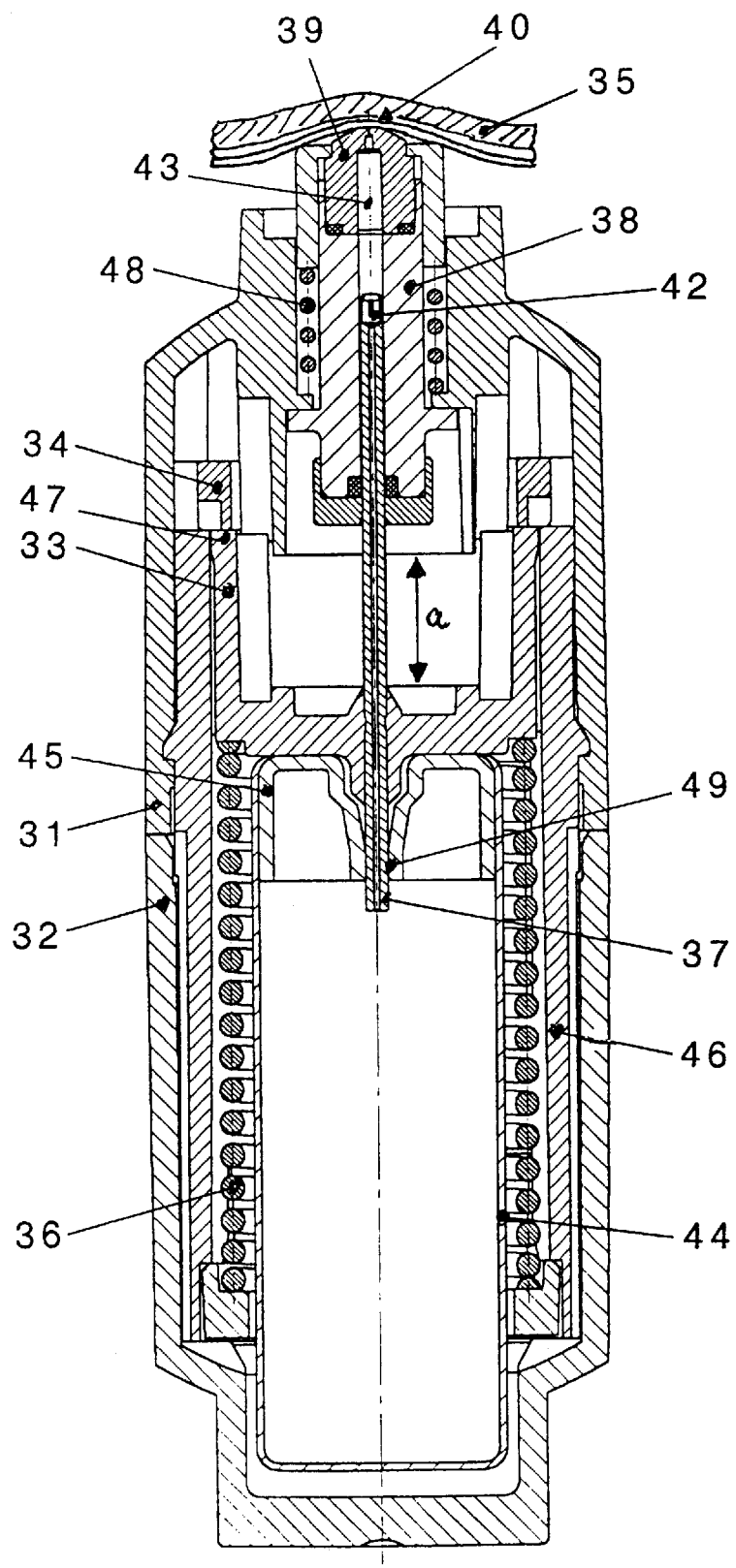
FIG. 2 is a sectional view of the needle-less injector of FIG. 1 in a stressed condition.

The invention will now be described in greater detail with reference to the Figures. FIG. 1 is a view in longitudinal section through a needle-less injector with triggering button, in the rest condition, in which the cylinder is fixedly arranged in the one housing portion. FIG. 2 is a view in longitudinal section through a needle-less injector without triggering button in the stressed condition of the energy-storing spring, in which the cylinder is arranged displaceably in the one housing portion.

Referring to FIG. 1 shown therein are the two housing portions 1 and 2 which are releasably connected together and which are arranged rotatably relative to each other. Of the locking stressing arrangement which is in the rest condition, the Figure shows the sprung portion 3, the locking member 4 in the disengaged condition, the triggering button 5 which acts on the locking member, and the energy-storing coil spring 6 in the form of a compression spring. Embedded in the sprung portion 3 is the hollow plunger 7 which engages into the cylinder 8. Mounted to the end of the cylinder is the nozzle 9 with the nozzle opening 10. The filter 11 is disposed in front of the nozzle. The nozzle end of the hollow plunger is provided with the valve body 12. The pump chamber 13 is disposed between the valve body and the filter. The supply container 14 is arranged in the otherwise free space within the coil spring; it is fitted in the flange 15 on to the hollow plunger and is held on the hollow plunger by the press fit 19. The cage 16 which surrounds the coil spring is connected in positively locking relationship to the housing portion 1. The sprung portion 3 bears against the abutment 17. The nozzle is protected by the removable closure cap 18.

Referring to FIG. 2, shown therein are the two housing portions 31 and 32 which are releasably connected together and which are arranged rotatably relative to each other. Of the locking stressing mechanism in the stressed condition, the Figure shows the sprung portion 33, the locking member 34 in the engaged condition and the energy-storing coil spring 36 in the stressed condition. Fixed in the sprung portion 33 is the hollow plunger 37 which engages into the cylinder 38. Mounted at the end of the cylinder is the nozzle 39 having the nozzle opening 40. The nozzle end of the hollow plunger is provided with the valve body 42. The pump chamber 43 is disposed between the valve body and the nozzle. The supply container 44 is arranged in the otherwise free space within the coil spring; it is fitted in the flange 45 on to the hollow plunger and is held on the hollow plunger by the press fit 49. The cage 46 which surrounds the coil spring is connected in positively locking relationship to the housing portion 31. The sprung portion 33 bears against the abutment 47 on the engaged locking member 34. The cylinder 38 is arranged axially slidably in the housing portion 31; it is held in its rest position by the helical return spring 48 which acts as a compression spring. The cylinder 38 is provided with a triggering device (not shown) which disengages the locking member 34 as soon as the cylinder 38 is pushed into the housing portion 31 against the force of the return spring when the needle-less injector is pressed against the injection location. Reference (a) denotes the travel of the drive portion between the two abutments. The stroke movement of the hollow plunger is identical to that travel.

FIG. 2 shows the needle-less injector when ready for the injection. The nozzle 39 is pressed against the diagrammatically illustrated skin 35 which is held taut; upon being further pressed against the injection location the needle-less injector is triggered and the liquid is injected into the skin 35 from the pump chamber 43.

Figure 3:
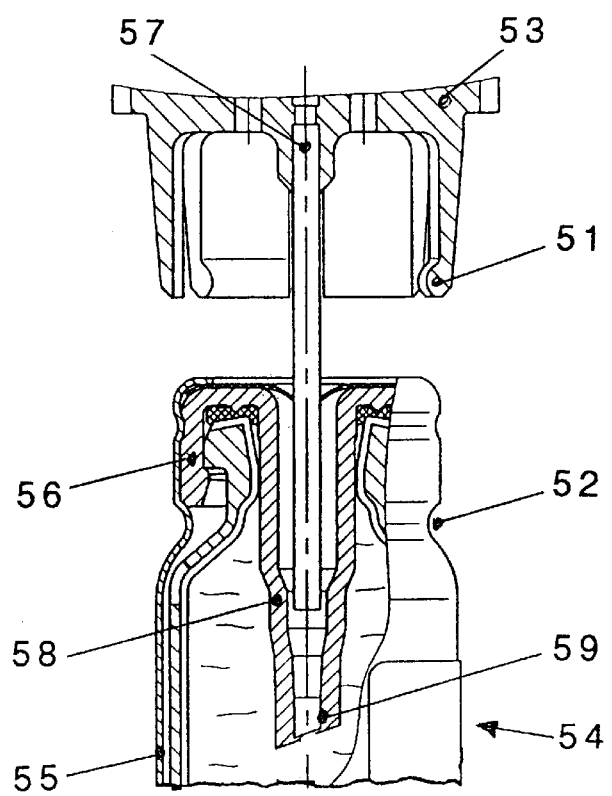
FIG. 3 is a sectional view of an end of a supply container and a sprung portion in an unengaged position in an embodiment of the invention.
Figure 4:
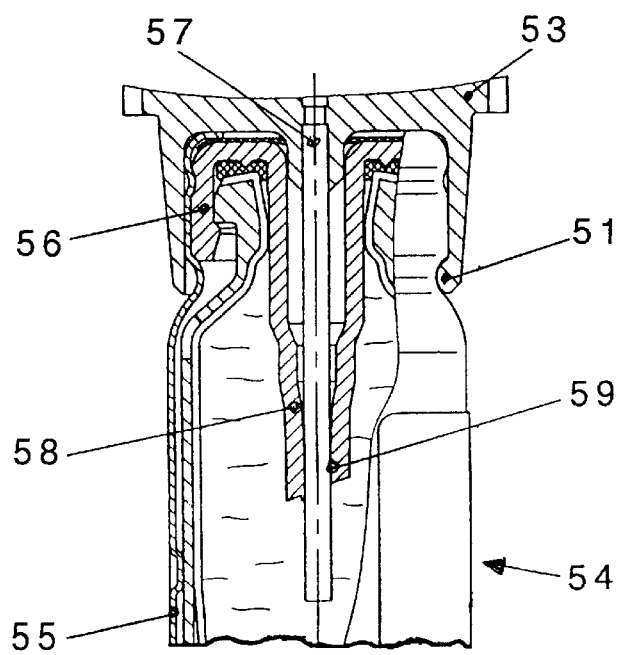
FIG. 4 is a sectional view of the supply container and sprung portion of FIG. 3 in engaged position.

FIGS. 3 and 4 show one end of the supply container and the sprung portion in a further embodiment. In FIG. 3 the hollow plunger has been introduced into the supply container but not yet connected to the hollow plunger.

FIG. 3 is a view in longitudinal section of part of the (triple-shell) supply container 54. The outer shell of the supply container is a stiff casing 55 which is provided with a peripherally extending groove 52. The supply container is closed by the plug 56 which goes into the immersion connection portion 58 with a press fit (59). A part of the sprung portion 53 with the hollow plunger 57 fixed therein is shown in longitudinal section. On its side towards the supply container the sprung portion is provided with a plurality of snap hooks 51.

In FIG. 4 the supply container is connected to the hollow plunger and the sprung portion, more specifically to the hollow plunger by the press fit 59 and to the sprung portion by way of the snap hooks 51 which engage into the peripherally extending groove 52 in the supply container.

The connection between the supply container and the sprung portion, which is shown in FIGS. 3 and 4, comprises snap hooks 51 with round shoulders and a peripherally extending groove 52 of semicircular cross-section. That connection is a releasable plug-in connection.

To provide a non-releasable plug-in connection, it is possible to adopt snap hooks with sawtooth-shaped shoulders and a peripherally extending groove of triangular cross-section.

EXAMPLE 1

Structure of a Needle-less Injector According to the Invention

A needle-less injector for intracutaneous injection into biological tissue has the following features:

The housing is of an outside diameter of about 20 mm and a length of about 70 mm. Both portions of the housing, the locking stressing mechanism and the spring cage, are made from polybutyleneterephthalate. The cylinder also comprises polybutyleneterephthalate; it is of an outside diameter of 5 mm and an inside diameter of 1.60 mm. The nozzle comprises quartz. The nozzle opening is of a diameter of 140 $\mu$m and a length of 220 $\mu$m. The hollow plunger of high-quality steel is of an outside diameter of 1.59 mm and an inside diameter of 0.35 mm. The piston stroke travel is 12 mm. The valve body comprises elastomer; it is in the form of a 2 mm thick disc with an outside diameter of 1.60 mm. The disc is provided on its peripheral surface with axial openings through which the liquid can flow past the valve body into the pump chamber. The end of the hollow plunger is provided with a groove into which the valve body engages. The amount of liquid expelled is about 23 mm$^3$. The interchangeable supply container is of a volume of about 11 cm$^3$.

EXAMPLE 2

Intracutaneous Application of a Liquid

An injection solution comprising 20 g of dextran fluorescein (UW 3000) per litre of distilled water was injected through the skin on two dogs under anaesthetic using the needle-less injector according to the invention. For that purpose 4.5 ml of the dextran fluorescein solution was introduced into the supply container of the needle-less injector and the supply container was connected to the hollow plunger of the injector. The injector was actuated by stressing and triggering the locking stressing mechanism a plurality of times in order to expel the air from the hollow plunger, the pump chamber and the nozzle. The needle-less injector was then applied to a previously shaved part of the skin in the region of the stomach of the dogs, and triggered. That procedure was repeated a plurality of times.

Blood samples were taken from the dogs at regular intervals, and the content of dextran fluorescein in the blood plasma was determined. The results demonstrate the operability of the needle-less injector according to the invention.

EXAMPLE 3

In Vitro Investigation of a Virus Suspension

Laboratory investigations using the needle-less injector were undertaken to ascertain whether the viability of suspended live viruses is reduced when the suspension is expelled through the nozzle of the needle-less injector.

The virus suspension which was collected after expulsion from the needle-less injector was found to involve a reduction by only about 1 $\log_{10}$ PFU (plaque forming units) with relatively large DNA viruses (test virus: Vaccinia virus) and by less (by about 0.5 $\log_{10}$ PFU) with small RNA-viruses (test virus: Bovine viral diarrhea virus).

EXAMPLE 4

In Vivo Application of a Vaccine with Modified Live Viruses

An animal test involved investigating the usability of the needle-less injector for administering a vaccine suspension with modified live viruses. In this investigation both the safety and the compatibility of a vaccination by means of a needle-less injector and also the effectiveness of this mode of administration were ascertained.

Six healthy dogs of the same age were put into two groups. Group 1 consisted of two dogs while group 2 consisted of four dogs. The animals of both groups were inoculated at a time interval in each case of three weeks, in each case on three occasions, with a modified live vaccine of the canine adeno virus.

In group 1, in each case 1 millilitre of the canine adeno virus vaccine (CAV-1) (Galaxy DA2ppvL+Cv, SNo 610041; Solvay Animal Health Inc) was administered intramuscularly in accordance with the manufacturer's recommendations by means of a hypodermic syringe. In group 2 an experimental canine adeno virus vaccine was administered by means of the needle-less injector.

The experimental vaccine (CAV-2) used for inoculation of the animals in group 2 was produced from a weakened strain of the canine adeno virus. The titer was 7.2 $\log_{10}$ TCID$_{50}$ per 60 microlitres (TCID=tissue culture infective dose). Six individual shots were administered at each inoculation point (six times 10 microlitres=60 microlitres for each inoculation). The injection region on the backs of the dogs was shaved, and the respective six injection locations marked by means of a ballpoint pen.

The effectiveness of the inoculation was ascertained by determining the number of virus-neutralising antibodies in the serum of the dogs in each case three weeks after each inoculation.

Compatibility was ascertained by observing the injection locations six hours after the inoculation and then daily up to the conclusion of the animal test. The injection regions were photographed and the findings after feeling the injection locations were noted.

This test revealed the following: In the case of the animals in group 2 a very slight degree of reddening of the injection locations was to be found during the first 2 to 3 days. Temporary swelling lasting 1 to 2 days could only be detected by feel. This slight and certainly acceptable local reaction is very probably related to the local amplification of the modified live virus administered and is therefore to be deemed necessary for the good effectiveness of the vaccine. This explanation is supported by the fact that, after the injection of physiological saline solution using the needle-less injector, no colouring whatsoever and no temporary swelling, even only slight, were to be noted.

The effectiveness was ascertained by the virus neutralisation test. The results are set forth in Table 1. The greatest titers are still capable of neutralising canine adeno virus.

Virus-neutralising antibodies were detected in the serum of all animals from both groups three weeks after the first inoculation. A slight reinforcement effect was found after the second and third inoculations.

Inoculation with the experimental canine adeno virus vaccine by means of the needle-less injector is just as effective as intramuscular inoculation with the commercially available vaccine by means of a hypodermic syringe.

TABLE 1

Canine adeno virus; virus neutralisation titer of canine serum

| Dog | | VN-titer of canine serum | | |
|---|---|---|---|---|
| Test No | Identification | 21 days after first inoculation | 21 days after second inoculation | 21 days after third inoculation |
| CAV-1 Commercially available vaccine intramuscularly by means of hypodermic syringe | | | | |
| 1496 | — | 1024 | 1024 | 4096 |
| 1498 | — | 1024 | 1024 | 512 |
| CAV-2 Experimental vaccine subcutaneously by means of needle-less injector | | | | |
| 1494 | TTK9 | 4096 | 4096 | 8192 |
| 1495 | USK9 | 4096 | 4096 | 8192 |
| 1497 | UVL9 | 4096 | 8192 | 4096 |
| 1499 | TVL9 | 2048 | 2048 | 2048 |

What is claimed is:

1. A hand-held, needle-less injector for a liquid, the needle-less injector comprising:
    a housing including at least two portions rotatable relative to each other;
    a cylinder disposed within said housing;
    a locking stressing mechanism disposed within said housing, said locking stressing mechanism including,
        a sprung portion, and
        a hollow plunger having a first end and a second end, said hollow plunger being fixed to said sprung portion, wherein said hollow plunger slidably extends within said cylinder, and wherein said hollow plunger includes a valve body disposed at said first end of said hollow plunger;
    a nozzle having one opening, said one opening having a hydraulic diameter in the range of 10 μm to 500 μm and said one opening having a length in the range of 50 μm to 500 μm, said nozzle being fixed to said cylinder such that said nozzle, said cylinder and said valve body form a pump chamber therebetween; and
    a removable supply container disposed within said housing, said supply container being connected around said second end of said hollow plunger, wherein an amount of a liquid conveyed from said supply container, through said hollow plunger into said pump chamber is determined by a stroke travel distance and a cross-section of said hollow plunger.

2. The needle-less injector according to claim 1, wherein said two portions of said housing are releasably connected together.

3. The needle-less injector according to claim 1 wherein said one opening has a hydraulic diameter in the range of 50 μm to 150 μm and said one opening is of a length in the range of 100 μm to 300 μm.

4. The needle-less injector according to claim 1, wherein said nozzle includes a plurality of nozzle openings.

5. The needle-less injector according to claim 4, wherein said plurality of nozzle openings have longitudinal axes extending in mutually parallel relationship or inclined divergently relative to each other.

6. The needle-less injector according to claim 1, wherein said housing includes an adjustable abutment extending therefrom for determining said stroke travel distance, such that said stroke travel distance of said hollow plunger is varied by said adjustable abutment.

7. The needle-less injector according to claim 1, wherein said locking stressing mechanism is stressed by rotating the two housing portions relative to each other by hand.

8. The needle-less injector according to claim 7, wherein said locking stressing mechanism is stressed by rotation of the two housing portions relative to each other to acuate a worm-thrust transmission.

9. The needle-less injector according to claim 1, wherein said locking stressing mechanism further comprises an energy storage means selected from the group of a coil spring, a disk spring and a leaf spring.

10. The needle-less injector according to claim 1, wherein said nozzle is comprised of metal, plastics material, glass, silicon or precious stone such as sapphire, ruby or corundum.

11. The needle-less injector according to claim 1, wherein said removable supply container is a replaceable supply container and said sprung portion receives said removable supply container.

12. The needle-less injector according to claim 1, wherein said removable supply container is releasably connected around said second end of said hollow plunger and is displaceable with the stroke movement of the hollow plunger within the housing.

13. The needle-less injector according to claim 12, wherein said removable supply container includes a peripheral groove and wherein said sprung portion is provided with snap hooks which releasably engage into said peripheral groove of said removable supply container.

14. The needle-less injector according to claim 1, further comprising a removable closure cap around said nozzle.

15. The needle-less injector according to claim 1, further comprising a filter disposed adjacent said nozzle in said pump chamber.

16. The needle-less injector according to claim 1, wherein said removable supply container contains a liquid medicament.

17. The needle-less injector according to claim 16 wherein said liquid medicament is selected from the group consisting of analgesics, vaccines, anti-diabetic agents, hormones, contraceptives, vitamins, antibiotics, sedatives, antimicrobial substances, amino acids and coronary agents.

18. The needle-less injector according to claim 1 wherein said sprung portion is displaceable between two abutments.

19. The needle-less injector according to claim 1 wherein said sprung portion is provided with a triggering device.

20. The needle-less injector according to claim 1 wherein said sprung portion is driven by said locking stressing mechanism.

21. The needle-less injector according to claim 1 wherein said supply container is connected around said second end of said hollow plunger by a press fit.

22. Use of the needle-less injector according to claim 1 for the injection of an active substance-bearing liquid into biological tissue.

23. Use of the needle-less injector according to claim 1 for the injection of an active substance-bearing liquid into vegetable tissue.

24. Use of the needle-less injector according to claim 1 for the injection of an active substance-bearing liquid into animal tissue.

25. Use of the needle-less injector according to claim 1 for the intracutaneous injection of vaccines into an animal.

26. Use of the needle-less injector according to claim 1 for the subcutaneous injection of vaccines into an animal.

27. Use of the needle-less injector according to claim 1 for the intracutaneous injection of vaccines into a human being.

28. Use of the needle-less injector according to claim 1 for the subcutaneous injection of vaccines into a human being.

29. Use of a needle-less injector according to claim 1 for the injection of a liquid through a membrane into the space behind the membrane.

30. A hand-held needle-less injector for a liquid, the needle-less injector comprising:

a housing including at least two portions releasably connected together and rotatable relative to each other;

a cylinder disposed within said housing;

a locking stressing mechanism disposed within said housing, said locking stressing mechanism, including, a sprung portion having snap hooks extending therefrom;

a coil spring biasing said sprung portion, and a hollow plunger having a first end and a second end, said hollow plunger being fixed to said sprung portion, wherein the hollow plunger displacably extends within said cylinder, and wherein said hollow plunger includes a valve body disposed at said first end of said hollow plunger;

a nozzle having a single opening, said opening having a hydraulic diameter in the range of 10 $\mu$m to 500 $\mu$m and said opening having a length in the range of 50 $\mu$m to 500 $\mu$m, said nozzle being fixed to said cylinder such that said nozzle, said cylinder and said valve body form a pump chamber therebetween;

a removable supply container disposed within said housing, said removable supply container being connected around said second end of said hollow plunger, and wherein said removable supply container includes a peripheral groove which engages said snap hooks of said sprung portion, wherein a liquid drug disposed in said removable supply container.

31. The hand-held needle-less injector according to claim 30 wherein said removable supply container is connected around said second end of said hollow plunger by means of a press fit.

32. Use of the needle-less injector according to claim 30 for the injection of an active substance-bearing liquid into biological tissue.

33. Use of the needle-less injector according to claim 30 for the injection of an active substance-bearing liquid into vegetable tissue.

34. Use of the needle-less injector according to claim 30 for the injection of an active substance-bearing liquid into animal tissue.

35. Use of the needle-less injector according to claim 30 for the intracutaneous injection of vaccines into an animal.

36. Use of the needle-less injector according to claim 30 for the subcutaneous injection of vaccines into an animal.

37. Use of the needle-less injector according to claim 30 for the intracutaneous injection of vaccines into a human being.

38. Use of the needle-less injector according to claim 30 for the subcutaneous injection of vaccines into a human being.

39. Use of a needle-less injector according to claim 30 for the injection of a liquid through a membrane into the space behind the membrane.

* * * * *

UNITED STATES PATENT AND TRADEMARK OFFICE
CERTIFICATE OF CORRECTION

PATENT NO. : 6,689,092 B2
DATED : June 1, 2005
INVENTOR(S) : Zierenberg et al.

It is certified that error appears in the above-identified patent and that said Letters Patent is hereby corrected as shown below:

Title page,
Item [*] Notice, please add, -- Subject to any disclaimer, the term of this patent is extended or adjusted under 35 U.S.C. 154(b) by 55 days. --

Signed and Sealed this

Nineteenth Day of July, 2005

JON W. DUDAS
*Director of the United States Patent and Trademark Office*